US011311310B2

(12) United States Patent
Valnicek (10) Patent No.: US 11,311,310 B2
(45) Date of Patent: Apr. 26, 2022

(54) FIXED DEPTH SKIN FLAP ELEVATOR DEVICE AND A METHOD OF USING THE SAME

(71) Applicant: Stanley Michael Karl Valnicek, Kelowna (CA)

(72) Inventor: Stanley Michael Karl Valnicek, Kelowna (CA)

( * ) Notice: Subject to any disclaimer, the term of this patent is extended or adjusted under 35 U.S.C. 154(b) by 421 days.

(21) Appl. No.: 15/978,409

(22) Filed: May 14, 2018

(65) Prior Publication Data
US 2018/0325542 A1  Nov. 15, 2018

Related U.S. Application Data

(60) Provisional application No. 62/506,323, filed on May 15, 2017.

(30) Foreign Application Priority Data

May 15, 2017 (CA) ................................. CA 2967150

(51) Int. Cl.
*A61B 17/322* (2006.01)
*A61B 17/00* (2006.01)
*A61B 17/32* (2006.01)

(52) U.S. Cl.
CPC .. *A61B 17/322* (2013.01); *A61B 2017/00796* (2013.01); *A61B 2017/320052* (2013.01)

(58) Field of Classification Search
CPC .......... A61B 17/32093; A61B 17/3211; A61B 17/322; A61B 2017/320052; A61B 2017/32113; A61B 2017/32116; G01N 1/06; G01N 2001/061; A61F 9/0133; A22B 5/168; A47J 17/02; A47J 17/04; Y10T 83/937; Y10T 83/9498; B26B 3/03; B26B 5/007; B26D 3/282; B26D 2003/285
USPC .......................................................... 30/305
See application file for complete search history.

(56) References Cited

U.S. PATENT DOCUMENTS

| 5,653,726 | A | 8/1997 | Kieturakis |
| 7,442,192 | B2 | 10/2008 | Knowlton |
| 8,753,339 | B2 | 6/2014 | Clark, III et al. |
| 8,858,544 | B2 | 10/2014 | McNally et al. |
| 9,078,688 | B2 | 7/2015 | Clark, III et al. |
| 10,531,768 | B1 * | 1/2020 | Brandt ..................... B26D 3/24 |
| 2004/0049251 | A1 | 3/2004 | Knowlton |

(Continued)

FOREIGN PATENT DOCUMENTS

WO    1985001431    4/1985

*Primary Examiner* — Thomas McEvoy
(74) *Attorney, Agent, or Firm* — Antony C. Edwards (57) ABSTRACT

A fixed depth skin flap elevator device is provided. The device includes an elongated handle having a proximal end and a distal end. The device further includes an upper arm and lower arm mounted to, so as to extend longitudinally from, the distal end of the handle. The upper arm overlays the lower arm. At least free ends of the upper and lower arms are spaced apart by a distance which is equal to a pre-determined cutting depth. A blade is supported on the lower arm at about its free end. Translation of at least the lower arm within a tissue interior results in separation of a deeper tissue from a surface tissue at a pre-determined cutting depth to form an undermined skin and subcutaneous surface tissue flap of uniform thickness. A method of using the device is also provided.

20 Claims, 7 Drawing Sheets

(56) References Cited

U.S. PATENT DOCUMENTS

| | | | |
|---|---|---|---|
| 2005/0131434 A1* | 6/2005 | Peyman | A61F 9/0133 |
| | | | 606/166 |
| 2006/0229648 A1* | 10/2006 | Dan | A61F 9/0133 |
| | | | 606/166 |
| 2008/0243158 A1 | 10/2008 | Morgan | |
| 2008/0249526 A1 | 10/2008 | Knowlton | |
| 2012/0073414 A1* | 3/2012 | Summo | B26D 1/06 |
| | | | 83/13 |
| 2016/0228143 A1 | 8/2016 | Pomahac et al. | |

* cited by examiner

FIXED DEPTH SKIN FLAP ELEVATOR DEVICE AND A METHOD OF USING THE SAME

CROSS REFERENCE TO RELATED APPLICATIONS

This application claims priority from U.S. Provisional Patent Application No. 62/506,323, filed on May 15, 2017, entitled "FIXED DEPTH SKIN FLAP ELEVATOR DEVICE AND A METHOD OF USING THE SAME" and Canadian Patent Application No. 2,967,150, filed on May 15, 2017, entitled "FIXED DEPTH SKIN FLAP ELEVATOR DEVICE AND A METHOD OF USING THE SAME", entireties of which are incorporated herein by reference.

FIELD

Embodiments described herein relate to a fixed depth skin flap elevator device and method of using same, for example for developing a plane of dissection at a controlled depth below the skin.

BACKGROUND

Elevation of skin and subcutaneous tissue at a predetermined and consistent depth is a common challenge during surgery. It is encountered most often with breast surgery (mastectomy) but also during a variety of other procedures including facial aesthetic surgery and the harvest of full thickness skin grafts. Current devices exist for elevation of skin at different depths (dermatomes) for the purpose of harvesting partial thickness skin grafts. The device described herein addresses the next layer down (the subcutaneous fat layer) and allows simpler and faster dissection at a controlled depth in a plane in the subcutaneous fat layer.

Treatment of breast cancer often includes surgery to remove breast tissue believed or proven to be cancerous. Various surgical procedures may be used. Such surgical procedures may include removal of a portion of the breast (partial mastectomy or lumpectomy), or if needed, removal of the entire breast (mastectomy).

Mastectomy leaves a cavity or pocket in the breast interior corresponding to at least the volume of breast tissue that has been removed. During mastectomy surgery, an attempt is made to accurately and evenly separate the breast tissue from the overlying skin and subcutaneous fat layer. Skin flap elevation, during mastectomy, must be performed in a precise plane preserving the full thickness of the skin and a certain desired thickness of underlying fat or the subcutaneous fat. However, this tissue plane is not always clearly distinct. Current technology to separate the two components utilizes devices with small leading points such as conventional scalpel blades or electrocautery tips. These devices have no intrinsic features that allow accurate and consistent control of the undermining depth, and thus the depth of the undermining can vary significantly as the flaps are elevated.

Depth control in undermined mastectomy skin flaps is important at least for the following reasons:
  Too thin a skin flap leads to poor or terminally compromised blood flow and delayed healing or tissue necrosis (partial or total flap loss).
  Too thick a skin flap leads to the potential of incomplete breast tissue removal which compromises the oncologic benefit of the surgery.
  Uneven skin flap thickness leads to a combination of the above-stated problems as well as irregularity (cobblestoning) of the surface in cases of reconstruction (rebuilding a new breast with implants or other means).

To summarize, uneven depth in mastectomy skin flaps may lead to significant wound healing issues resulting in increased patient suffering, prolonged hospitalization, extended outpatient wound care needs and frequent re-operation. Also, the potential for local recurrence of cancer may be elevated if the skin flaps are too thick and the breast tissue is incompletely resected. Further, aesthetic outcomes of subsequent reconstructive surgery may be compromised from "cobblestoning" or dimpling of the skin or partial scarification due to uneven undermining. Little can be done effectively to restore the normal breast contour if the thickness of the remaining healthy tissue of the breast is too thin and not uniform. Consequently, the resulting deformity may be permanent. This ultimately leads to undue burden on the healthcare system and an unnecessary decrease in quality of life for the patient post a mastectomy procedure.

It has proven difficult to excise breast tissue while maintaining a uniform thickness of healthy tissue surrounding the mastectomy space. Medical instruments such as dermatomes are known to harvest sheets of skin at controlled depths for use as split thickness skin grafts. Dermatomes are surface cutting instruments that are hand or mechanically powered with a blade that oscillates side to side. Dermatomes include an adjustment for depth of harvest. However, dermatomes are not intended for cutting through the fatty layer located deep under the skin. The harvested skin graft is fed through the device while limiting the width of the graft to the device width as the side edges of the skin are cut free. Dermatomes are thus designed to elevate partial thickness skin sheets and not undermine tissue.

Consequently, there is a need for a device, and corresponding method employing the device, which may simplify surgical excision of unhealthy or target breast tissue while maintaining substantially uniform thickness of healthy tissue surrounding a mastectomy space. In other words, there is a need for a device for creating a mastectomy skin flap of even or uniform thickness. This device design could also be utilized in facial aesthetic surgery where predictable and even undermining of the skin of the cheek or neck is essential as well as in harvesting full thickness skin grafts in the plane immediately beneath the dermis.

SUMMARY

Embodiments described herein relate to a fixed depth skin flap elevator device and a method of using the same. The device enables improved control and consistency in the depth of undermining of a skin flap in circumstances where skin and a specific thickness of attached (subcutaneous) fat is to be separated from the underlying tissue. In breast surgery, a mastectomy skin flap of even or uniform thickness is desirable in circumstances where a tumor does not encroach on the subcutaneous layer. This enables consistent blood flow to the remaining tissues which enhances general healing, minimizes patient complications and suffering, saves health care costs and provides a smoother contour for future reconstruction. In aesthetic facial surgery, an even thickness of fat under the skin minimizes risk to deeper structures such as sensory and motor nerves while maintaining more consistent blood supply and smoother contour. In full-thickness skin graft harvest, the device would provide an even depth of subdermal undermining with less risk of buttonholing (cutting up through) the graft and less blunt crush injury to the graft interface from scissors or other instruments.

The device described herein is a simple hand held device that allows even skin and fat flap undermining at a preselected depth below the surface of the skin.

Accordingly, in one broad aspect, a fixed depth skin flap elevator device for undermining and raising a flap of skin and subcutaneous surface tissue at a consistent and controlled depth from a tissue interior is provided. The tissue interior includes the surface tissue overlaying a deeper tissue. The device includes an elongated handle having a proximal end and a distal end. The device further includes an upper arm and lower arm mounted to, so as to extend longitudinally from, the distal end of the handle, the upper arm overlaying the lower arm. At least free ends of the upper and lower arms are spaced apart by a distance which is equal to a pre-determined cutting depth. A blade is supported on the lower arm at about its free end. Translation of at least the lower arm within the tissue interior results in separation of the deeper tissue from the surface tissue at the pre-determined cutting depth to form an undermined skin and subcutaneous surface tissue flap of uniform thickness.

Accordingly, another broad aspect, a fixed depth skin flap elevator device is provided. The device includes a blade holder having a first structural frame lying substantially in a first plane. The first frame has a first end and an opposite second end longitudinally spaced apart on said blade holder. The device further includes a guide having a second structural frame. The second frame has opposite first and second ends. The second structural frame overlays the first structural frame so as to define a spacing gap between at least said first ends of said first and second structural frames. The device further includes a handle mounted to the second end of the first and second structural frames. A cutting blade is mounted to, so as to extend across, said first end of said first frame, substantially in the first plane. The spacing gap corresponds to a predetermined fixed depth for cutting by the blade subcutaneous tissue below a skin surface in contact with at least the first end of the second frame.

Accordingly, in another broad aspect, a method for assisting in even separation of skin and subcutaneous surface tissue from an underlying deeper tissue is provided. The method includes manipulating a proximal end of an elongate shaft of a skin elevator device to deploy a lower arm of the device at a preselected cutting depth within the surface tissue and to locate an upper arm in parallel relationship with said lower arm against an outside surface of skin surrounding the breast interior. The method further includes advancing the lower arm through the surface tissue at the preselected cutting depth by manipulating the proximal end of the shaft for evenly separating the layer of skin and a desired thickness of the surface tissue from the deeper tissue so as to create an undermined skin and surface tissue flap of uniform thickness.

BRIEF DESCRIPTION OF THE DRAWINGS

FIGS. 7A to 7D are schematic views illustrating various use positions of the device of FIG. 2, wherein.

DETAILED DESCRIPTION

An apparatus and method for excising tissue using a fixed depth skin flap elevator device are described herein. The device may be used to improve skin flap undermining during breast surgery (mastectomy), facial surgery and full thickness skin graft harvest by helping maintain a relatively constant and even depth of dissection. In breast surgery this facilitates separation of a layer of skin and healthy subcutaneous fat from the underlying breast tissue. In facial and neck surgery, this helps elevate skin and subcutaneous tissue flaps with less risk of perforating the skin or injuring deeper structures. Even undermining of skin/fat flaps facilitates blood flow and healing of the wounds as well as separating tissues at a consistent depth determined by the operator.

In mastectomy surgery, the target tissue is typically located at a certain depth within an interior of a breast. The depth can vary, and in severe cases a tumor might penetrate up through the surface of the skin. This device is intended for use when there is a layer of healthy tissue in the subcutaneous fat layer separating the skin and the target tissue by enough distance to enable the device to create a plane of separation between the two. Traditionally, a surgeon will determine the depth of the flap undermining based on patient factors (age, skin thickness, thickness of subcutaneous fat layer among others) as well as target tissue proximity to the subcutaneous fat layer. This depth is then cut with devices such as scalpel, scissors or cautery which provide the ability to constantly adjust the depth of the cut but are difficult to maintain at an even depth when this is desired. The present device is intended to complement traditional cutting devices in circumstances where the surgeon wishes an even and predictable depth of skin flap undermining. A range of fixed depths on the device will allow the surgeon to choose a depth that matches the clinical needs of the patient situation.

Figure 1:
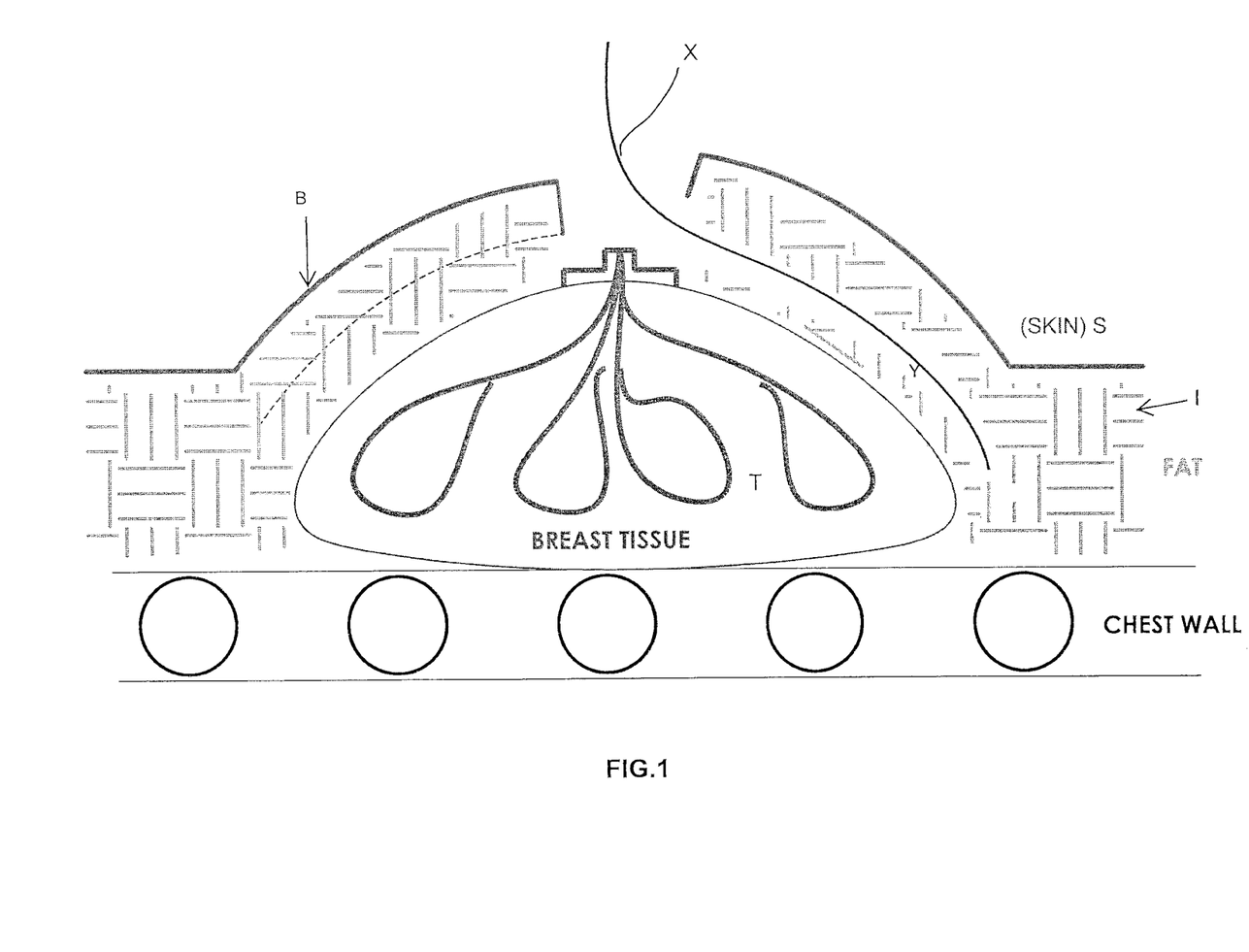
FIG. 1 is a schematic view of a breast illustrating a target tissue located at a depth within an interior of the breast.
Figure 2:
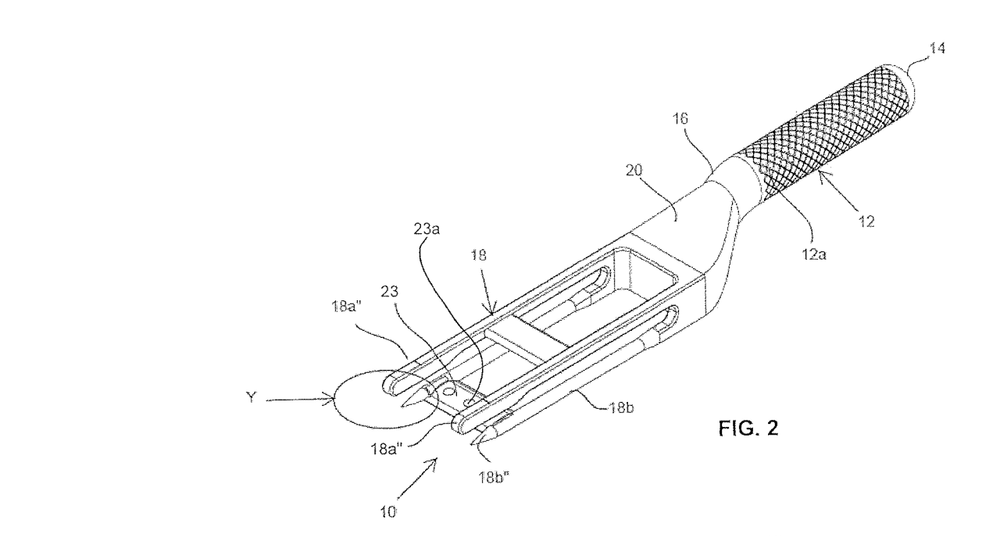
FIG. 2 is a side perspective view of one embodiment of a fixed depth skin flap elevator device.

As seen in FIG. 1, target tissue T is located within an interior I of a breast B at a thickness or depth. The target tissue T is surrounded by healthy tissue H in the subcutaneous fat layer which in turn is surrounded and encapsulated by overlying skin S. Based on the location of the target tissue T, a depth of a dissection plane is determined so as to leave a desired thickness of healthy tissue H adhered to the skin S after the mastectomy procedure. The depth of the dissection plane is referred to as depth D herein. The dissection plane depth D is interchangeably referred to herein as a pre-determined cutting depth. The dissection plane is denoted by "X" and is also shown in FIGS. 1 and 7B in the accompanying drawings. "Healthy tissue" and "target tissue" are also interchangeably referred to herein as "surface tissue" and "deeper tissue", respectively.

As stated in the foregoing paragraphs, creation of a dissection plane that is too shallow may produce tissue necrosis due to interruption of the blood supply to the skin. Creating of a dissection plane which is too thick may result in incomplete removal of the target tissue T. The device disclosed herein evenly separates the target tissue T from the healthy tissue H so as to create an evenly or uniformly undermined skin flap.

FIGS. 2 to 6 illustrate one embodiment of a fixed depth skin flap elevator device for separating target tissue T from healthy tissue H at a pre-determined cutting depth within a subcutaneous tissue interior such as breast interior I. Device 10 includes an elongate shaft 12 which serves as a handle. Shaft 12 may have other shapes than as illustrated in FIGS. 2 to 6. For example, shaft 12 may be a combination of shapes to improve grip, balance, and tactile feedback to a surgeon. Shaft 12 has a proximal end 14 and a distal end 16, proximal and distal in the sense that, in use, the proximal end may be closest to the surgeon using the device 10. As illustrated, shaft 12 may comprise an enhanced gripping surface 12a, which may include ridges, depressions, protuberances, portions which have an increased co-efficient of friction, or other means known in the art which enhance and facilitate controlled manipulation of the device 10 during its use or operation by a surgeon.

Figures 3, 4:
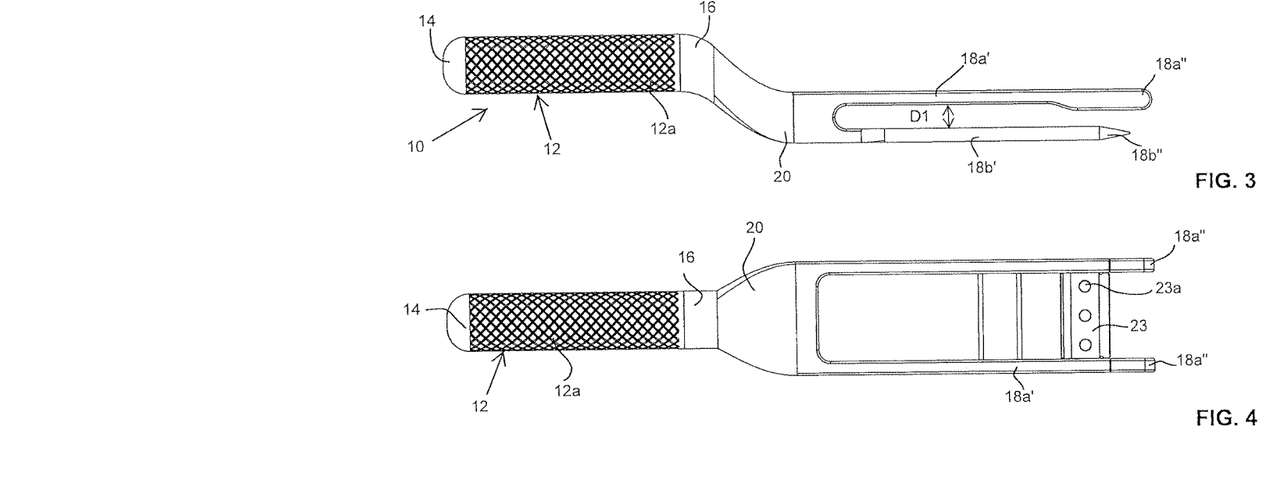
FIG. 3 is a side view of the device of FIG. 2.
FIG. 4 is a top view of the device of FIG. 2.
Figure 6:
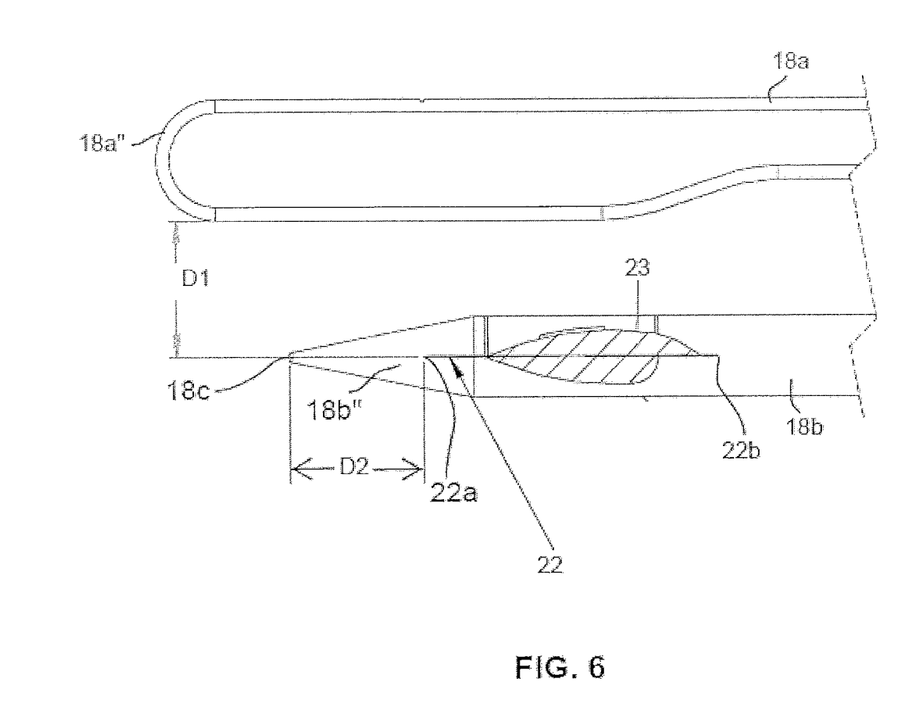
FIG. 6 is an enlarged view of the portion marked Y in FIG. 2, the view being enlarged to show configuration of the free ends of upper and lower arms of the device.

Arms 18 extend forwardly from shaft 12. In the illustrated embodiment, which is not intended to be limiting, arms 18 include a pair of parallel arms, disposed as left and right arms 18 forming a fork extending from shaft 12. Each of left and right arms 18 have an upper arm 18a and a lower parallel arm 18b. The upper and lower arms 18a and 18b are mounted to a neck 20 formed at the distal end 16 of shaft 12. Neck 20 forms the base of the fork and supports arms 18. Each upper arm 18a overlies its corresponding lower arm 18b, when device 10 is held in the orientation of FIG. 2. In that view, each upper arm 18a is vertically separated from the corresponding lower arm 18b by a distance or gap D1 as seen in FIGS. 3 and 6. Gap D1 is not less than the pre-selected cutting depth D. In one embodiment, not intending to be limiting, each upper arm 18a and its corresponding lower arm 18b, are substantially parallel and each form a further U-shaped fork in conjunction with neck 20. For ease of reference, these forks are referred to as the left and right forks. In one embodiment, not intended to be limiting, the upper and lower arms 18a and 18b, respectively each have corresponding mid-arm sections 18a' and 18b' extending longitudinally from neck 20 to tips or ends 18a" and 18b" respectively.

Lower arms 18b are a carrier for a blade and support a blade 22 such as a conventional rectangular, double-edged planar shaving blade such as sold by Wilkinson™. In the illustrated embodiment, not intended to be limiting, the blade 22 is supported on a contoured plate or cross-arm 24 extending laterally across and between the mid-arms 18b'. In the illustrated embodiment, not intended to be limiting, blade 22 is held clamped between the cross-arm 24 and a removable upper blade cover 23. Pins 23a extend upwardly from cross-arm 24 so as to engage through corresponding holes conventionally found on a Wilkinson™-style shaving blade. Pins 23a may extend upwardly sufficiently so as to extend through corresponding apertures in blade cover 23. For additional support, the ends 22' of the blade 22 may also be anchored into lower arms 18b. A leading edge 22a of the blade 22 protrudes from a front edge of plate or cross-arm 24. If the blade 22 is double edged, the leading edge 22a and a trailing edge 22b of the blade 22 may protrude from the cross-arm to be exposed between the lower arms 18b. This device could also utilize alternative commercially available or proprietary single and double edged blades with variance in width, rigidity and thickness.

In one embodiment, not intended to be limiting, tips or ends 18b" of the lower arms 18b extend forwardly beyond the leading edge 22a of the blade 22 by distance "D2" as seen in FIG. 6. Distance D2 may be substantially equal to the gap distance D1 to help maintain the cutting depth even when an upward (ascending) force is applied to the device 10 such as seen for example in FIG. 7C.

Figure 7A:
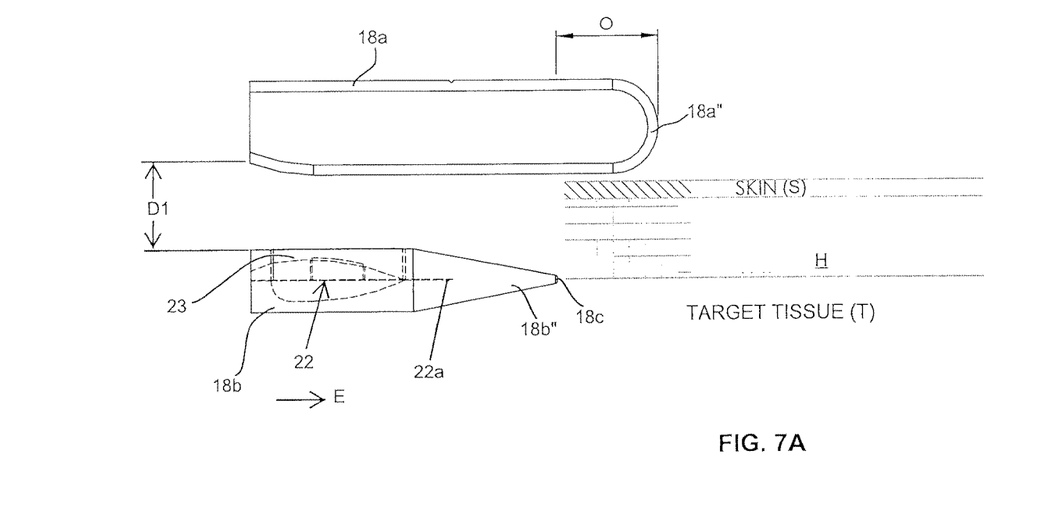
FIG. 7A illustrates location of the device in a start position.
Figure 7B:
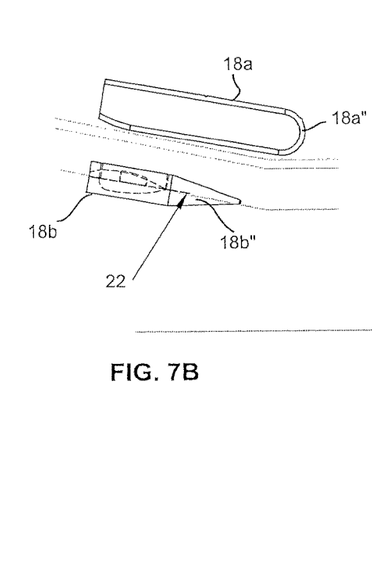
FIG. 7B illustrates a position of the device when a downward force is exerted thereon.

In one embodiment, the ends 18a" of the upper arm 18a extend beyond the ends 18b" of the lower arm 18b by a positive overhang distance "O" as seen in FIG. 7A. In other contemplated embodiments, the ends 18a" of the upper arm 18a may have a negative or a neutral overhang with respect to the ends 18b" of the lower arm 18b.

Figure 5:
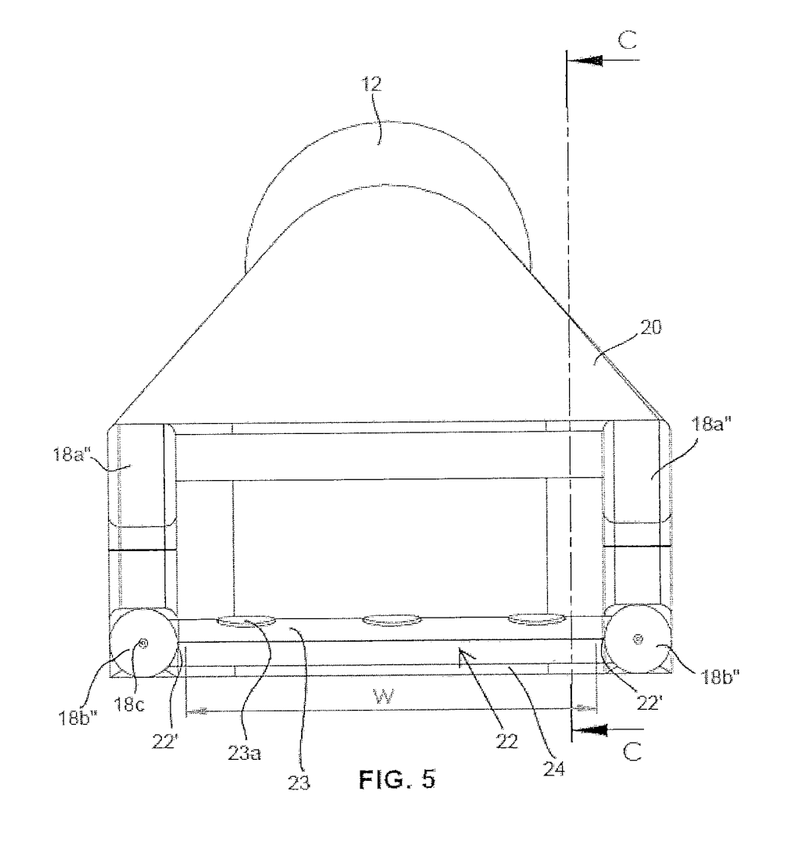
FIG. 5 is an end view of the distal end of the device of FIG. 2.
Figures 5A, 5B:
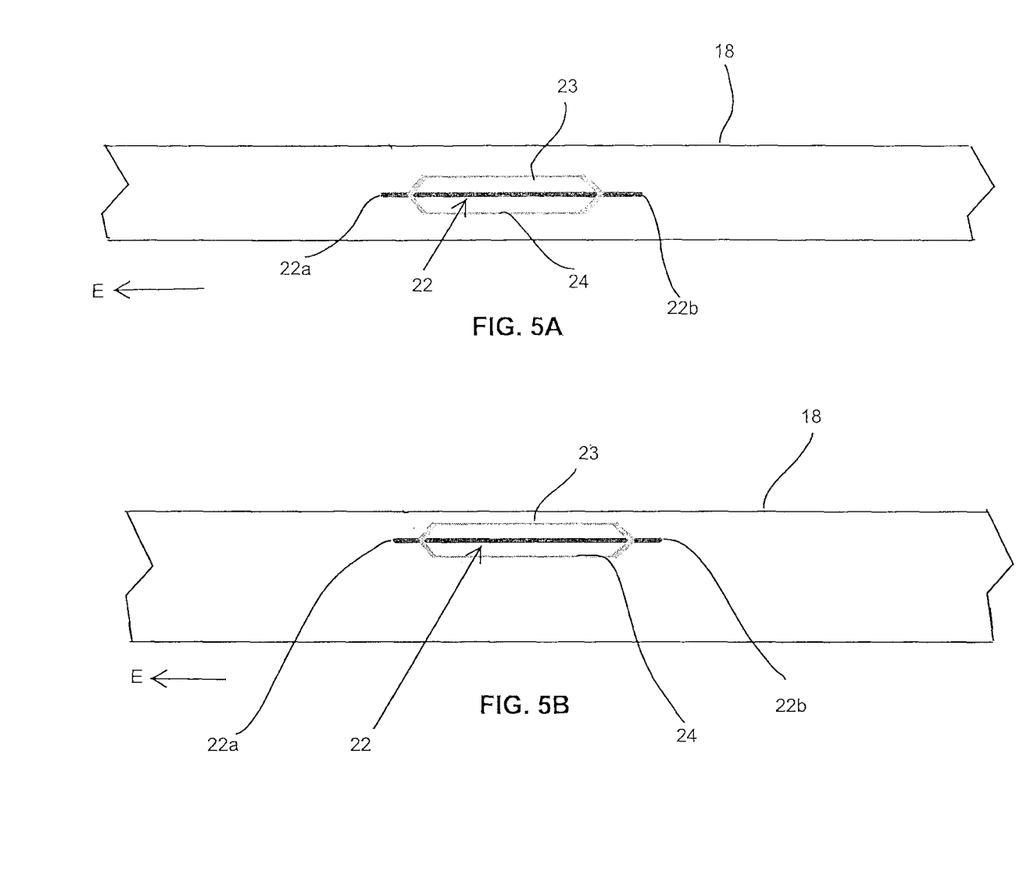
FIGS. 5A and 5B are schematic partial side views of a lower arm of the device of FIG. 2 illustrating alternative embodiments for positioning a blade of the device with respect to upper and lower surfaces of the lower arm.

In one embodiment and with reference to FIGS. 5A and 5B, the position of the blade 22 may be varied vertically between upper and lower surfaces of the lower arms 18b. FIG. 5A illustrates an embodiment where the blade 22 is centered between the upper and lower surfaces of the lower arm 18. FIG. 5B illustrates an embodiment where the blade 22 is supported closer to the upper surface of lower arm 18b.

Preferably, and as better seen in FIG. 6, ends 18b" of the lower arms 18b have points 18c that are sharp enough to pass forward through the subcutaneous fat and connective tissue (healthy tissue H around the target tissue T) but not so sharp as to penetrate the dermis of the overlying skin S when upward force is exerted on the device 10. Profile of the ends 18b" may vary from a sharp point to a rounded blunt tip depending on the use of the device and density of the subcutaneous fat layer. The ends 18a" of the upper arm 18a are smooth, for example bullet-nosed as illustrated, or otherwise rounded, or otherwise have upwardly curved lower surfaces so as to allow gliding over the surface of the skin S when downward and forward pressure is exerted on the device 10 such as seen for example in FIGS. 7B and 7C. Further, the ends 18a" have sufficient surface area to not substantially indent or penetrate the skin surface when downward (diving or descending) force is applied manually on the device 10.

In one embodiment the entire device 10 is disposable. In other embodiments only blade 22 is disposable. Preferably, shaft 12, neck 20, and upper and lower arms 18a and 18b, are of an unitary construction, made, for example, by injection molding or other techniques well known in the art. Alternatively, the components may be manufactured separately, and later affixed in position by assembly of the various components of device 10, for example in a kit form. In one embodiment, arms 18a and 18b, neck 20 and blade 22 may be a single disposable component, modularly interchangeable on a reusable shaft 12.

As stated above, on each of the left and right arms 18, the upper and lower arms 18a and 18b are separated by a gap distance D1 which is not less than the pre-determined cutting depth D. The corresponding gap distance D1 assists in positioning the lower arm 18b, and consequently the blade 22, adjacent healthy tissue H lying in the dissection plane X at the pre-determined desired cutting depth D.

FIGS. 7A-7D and the following paragraphs illustrate and describe use or operation of the device 10. FIG. 7A illustrates the initial position of the device 10. In the initial position, the ends 18a" of the upper arm 18a rest against the outside surface of skin S. Since the upper and lower arms are separated by the distance D1, which is equal to the pre-determined cutting depth D or depth of the dissection plane X, the lower arm 18b is deployed aligned with the dissection plane X with ends 18b" abutting healthy tissue H. As seen in FIG. 7A, the ends 18b" are aligned with an access site at the pre-determined cutting depth D for introduction of the ends 18b" into the subcutaneous healthy tissue (H) through a surgical incision at the access site. As one of skill in the art will understand, there may be multiple access sites so as to manipulate around the entirety of the tissue to be lifted around T.

Figure 7C:
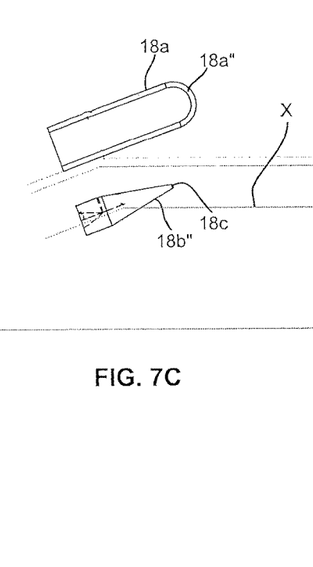
FIG. 7C illustrates a position of the device when a upward force is exerted thereon; and, FIG. 7D illustrates a position of the device when the device is translated generally parallel to a cutting or dissection plane.
Figure 7D:
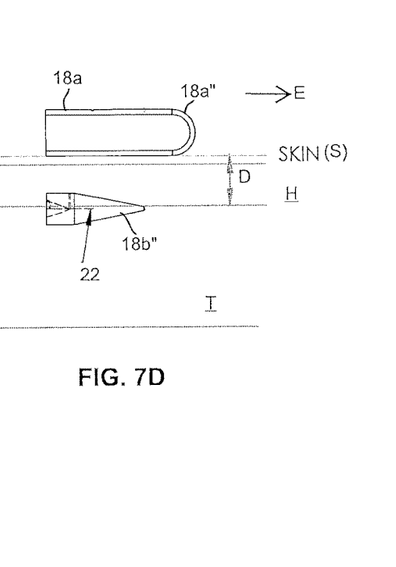

With reference to FIGS. 7B to 7D, blade 22 lies in the cutting or dissection plane X. Handle 12 is manipulated by the surgeon to advance the ends 18b" of the lower arm 18b and leading edge 22a of blade 22 in direction E through healthy tissue H lying in the dissection plane. As ends 18b" protrude forwardly of edge 22a, the cutting action of blade 22 is preceded by a piercing action as the points 18c of the ends 18b" of the lower arm 18b pierce through the subcutaneous tissue before the tissue is cut by blade 22. The pointed free ends 18b" of the lower arm 18b may facilitate forward travel or translation in direction E of the lower arm 18b through the subcutaneous interior I. If blade 22 is double edged, reversing direction may also be used to cut tissue, resulting in a reciprocating motion.

During manipulation of device 10, the lower arm 18b may be rotated about three orthogonal axes within the subcutaneous tissue interior I as required for cutting the desired skin flap.

FIG. 7B-7D show various positions attained by the upper and lower arms during manipulation of the device 10. FIG. 7B shows the position of the upper and lower arms 18a and 18b, respectively when a downward force at a downward angle of attack is exerted on the device 10. FIG. 7C shows the position of the upper and lower arms 18a and 18b, respectively when an upward force at an upward angle of attack is exerted on the device 10. FIG. 7D shows the position of the upper and lower arms 18a and 18b when the device is being translated with the guide arms 18a substantially flush along the skin S so that the blade 22 cuts along the dissection or cutting plane X.

In the case of mastectomy surgery, removal of target tissue T from the breast interior results in a cavity in the breast interior I. Since the cavity was created by cutting at a pre-determined uniform depth D, wall of cavity is of uniform thickness. Therefore, when an implant is placed within such a uniform-walled cavity, the implant makes contact with healthy tissue all along the contour of the cavity and supports the healthy tissue all along the contour of the cavity. This even support and uniform wall thickness is reflected topographically by the resulting uniform geometry of the breast post-surgery. Further, undermining at the pre-determined depth also ensures that the resulting skin and fat flap is of a consistent thickness which is neither too thin nor too thick. This significantly reduces the healing issues and incomplete removal of the target tissue issues outlined in the background.

As one of skilled in the art will understand, pre-determined cutting depth D will vary depending on the application, and in the case of a mastectomy, the depth D will vary depending on the location and size of the target tissue within the breast interior I. Accordingly, a range of models may be designed for different cutting depths.

Device 10 may include the following features:
  A fixed width that allows even undermining and which may be applied in multiple passes to extend the width of the area undermined.
  A range of depth options corresponding to a set of devices 10 each having a different gap D1 which would allow a surgeon to select a desired depth of dissection plane to match the application and the anticipated subcutaneous fat layer thickness in individual patients.
  A pair of upper guide arms may have positive overhang of the guide arm tip over the tips of the lower arms holding the blade, as illustrated, or wherein the overhang is negative (the guide tips are recessed behind the lower tips). A pair of lower, blade supporting arms, located under the pair of upper guide arms, and aligned vertically therewith, to hold a blade having at least a forward cutting edge such as leading edge 22a aligned for forward cutting when the device is pushed forwardly, wherein the forward cutting edge is set back from the tips of the lower arms by a setback distance (D2) substantially equal to the gap distance (D1) between the upper and lower arms.

The above described embodiments corresponding to the illustrations in FIGS. 2 to 6, are not intended to be limiting. Other embodiments are contemplated which would also fall within the scope of the present invention.

Figure 8:
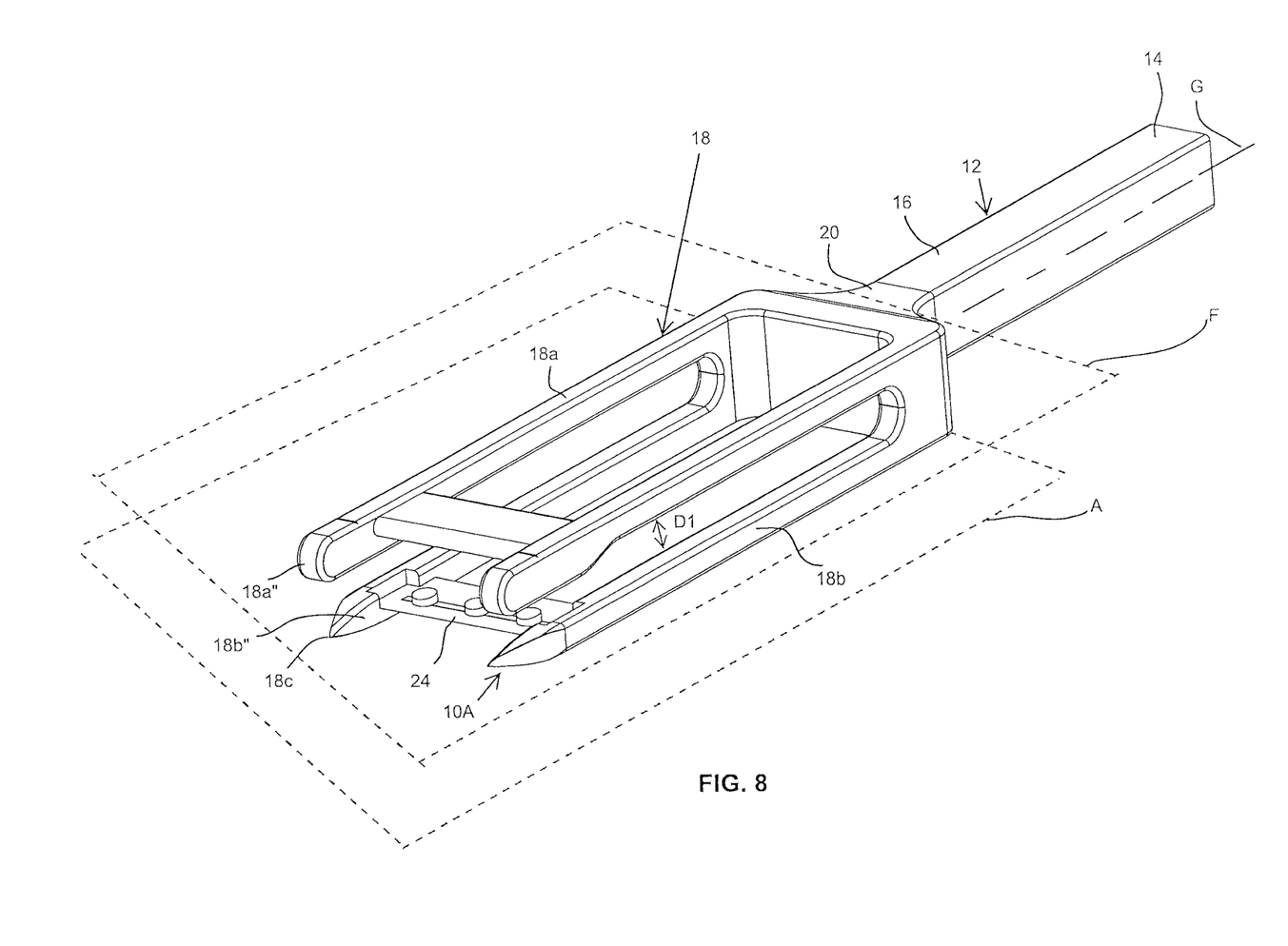
FIG. 8 is a side perspective view of another embodiment of a fixed depth skin flap elevator device.

Accordingly, FIG. 8 illustrates another embodiment of a skin flap elevator device. Device 10A illustrated in FIG. 8 is similar to the device 10 and functions substantially in a similar manner.

Similar components in device 10 and 10A are referred to herein using same reference numerals. The device 10A may be described as having the following elements; namely, (1) a handle 12, a pair of lower arms or blade holder arms 18b lying in plane A; (2) a pair of upper guide arm 18a lying in plane F, wherein the blade holder arms and guide arms are mounted to one end (distal end 16) of the handle; and, (3) a cutting blade 22 mounted to and between the pair of lower blade holder arms 18b aligned for cutting through tissue in the dissection plane X. The blade holder arms 18b may be described as a first structural frame lying substantially in a first plane, that being plane A. The guide arms 18a may be defined as a second structural frame lying in plane F. The second structural frame may be described as over-laying the first frame of the blade holder so as to define the gap distance D1 therebetween. If the first frame of the blade holder is described as having a first end and an opposite second end which is longitudinally spaced apart on the blade holder, for example, in the direction of the longitudinal axis G of handle 12, and the second frame of the guide is defined as having corresponding first and second opposite ends longitudinally spaced apart in plane F, then the gap D1 between the blade holder and guide may be more particularly described as being the gap between at least the first ends of the first and second frames.

Thus, the first frame of the blade holder supports the blade in the cutting plane at the predetermined distance D1 below the second frame, which acts as the guide, as the guide slides over the skin S of the flap to be undermined. Thus it will be understood that instead of being forked, in an alternative embodiment, the second frame may be a single continuous component extending laterally over the blade or may be some other structure such as a lattice-work so as to lend rigidity to the second frame and thus minimize flexing of the second frame which may adversely affect maintaining the uniform wall depth or thickness D.

Similarly, the blade holder or first frame may also be a solid unitary component supporting blade 22 in plane A or may be some other structure such as more than two longitudinally extending cantilevered arms or may be a lattice-work or such other structure lending rigidity to supporting blade 22 at a uniform spacing gap or distance D1, again to minimize flexing of the cantilevered support of blade 22 to maintain uniformity of thickness or depth D. The blade itself may be supported on a cross-arm or cross-arms extending between the forks of the blade holder to inhibit flexing or bending of the blade during use. The cross-arm or cross-arms may thus also lend rigidity to the first frame.

In further alternative embodiments, the first and second frames of respectively the blade holder and guide do not necessarily have to lie entirely within their respective planes A and F. For example, the ends 18b" and 18a" of respectively the blade holder and the guide may reside in planes A and F while their corresponding supporting structure of the first and second frames may curve out of their respective planes. For example, the second frame may be a curved structure extending from neck 20 to ends 18b" again so as to provide increased rigidity to the second frame.

Where the blade holder is a unitary or continuous structure extending laterally across dimension D2, blade 22 may for example be embedded in the leading edge of the first frame extending between ends 18c.

In further alternative embodiments, although opposing legs 18a" of the upper arm 18a are shown to be parallel to one another and laterally spaced apart, and similarly opposing legs 18b" of the lower arm 18b are shown to be parallel and laterally spaced apart, this need not be limiting as other geometries will also work. In the illustrated embodiments, opposing legs of the upper and lower arms are illustrated as lying in parallel, laterally spaced first and second vertical planes which are orthogonal to planes A and F. Again, other geometries will work. The laterally opposed legs of the forked arms do not need to be parallel to one another as for example they may define a V-shape line in planes A or F, or in some plane there between. Thus, the supporting structure for blade 22 may extend in a V-shape or u-shape or other such shape extending from the handle 12 so as to support blade 22 cantilevered from neck 20 by a desired cantilevered distance, overlaid by the second frame of the guide structure also cantilevered from neck 20 by the desired cantilevered distance.

Also, each arm does not need to be parallel to one another as for example the upper arm may be curved relative to the lower arm so as long as the ends of the upper and lower arms remain at the desired uniform gap spacing D1, and the leading edge 22a of blade 22 is set back from the corresponding tips 18c of the lower arm 18b by a distance (D2) which is substantially the same as gap distance D1.

The blade 22 might be exposed on the leading edge only, but advantageously on the leading and trailing edge of its mounting assembly, especially if the blade 22 is double edged.

In preferred embodiments, not intended to be limiting, gap D1 and length of the arms 18 may be as follows: gap D1 may be in the range from 3 mm to 3 cm; and the length may be in the range from 2 to 16 cm, or as desired by the surgeon to best work within the desired depth and extent of skin flap undermining. The handle 12 may be, for example, approximately 12 cm long. For mastectomies, the width of blade 22 (dimension W in FIG. 5) may be substantially the width of a conventional Wilkinson™ shaving blade. For facial surgery, the width of the blade may be half of that.

What is claimed is:

1. A fixed depth skin flap elevator device for undermining and separating an even and uniform flap of skin and healthy tissue, at a consistent and controlled depth, from a tissue interior, wherein the tissue interior is below a surface of the skin and includes at least the healthy tissue overlying a deeper tissue, the device comprising:

an elongated handle having a proximal end and a distal end;

an upper arm and lower arm mounted to, so as to extend longitudinally from, the distal end of the handle, the upper arm overlaying the lower arm, and wherein the upper and lower arms are forked along their length so as to define a pair of laterally opposing legs in each arm, and wherein at least free ends of the upper and lower arms are spaced apart by a distance which is equal to a predetermined cutting depth, and wherein, during operation of the device, the lower arm is adapted to be located within and translated through the tissue interior at the predetermined cutting depth, and wherein free ends of the opposing legs of the lower arm are adapted to pierce through the healthy tissue at the predetermined cutting depth to assist translation of the lower arm through the tissue interior; and a cutting blade rigidly mounted to so as to extend laterally relative to the lower arm and fixed relative to the lower arm at about the free end of the lower arm so as to lie, during operation of the device, in a dissection plane which is located in the tissue interior at the predetermined cutting depth, and wherein, during operation of the device, translation of the upper arm over the surface of the skin and translation of the lower arm below the surface of the skin within the tissue interior results in piercing and cutting of the healthy tissue and separation of the healthy tissue from the deeper tissue at the predetermined cutting depth to form the even and uniform flap of skin and healthy tissue.

2. The device of claim 1, wherein the blade is supported across the opposing legs of the lower arm.

3. The device of claim 1, wherein the free ends of the opposing legs of the lower arm protrude beyond a leading edge of the blade.

4. The device of claim 3, wherein the piercing action precedes the cutting action.

5. The device of claim 1, wherein free ends of the opposing legs of the upper arm have one of a negative, neutral or positive overhang with respect to the free ends of the opposing legs of the lower arm.

6. The device of claim 1, wherein free ends of the opposing legs in the upper arm are adapted to glide over skin overlying the healthy tissue while preventing indentation of the skin.

7. The device of claim 6, wherein the free ends of the opposing legs of the upper arm are blunt.

8. The device of claim 1 further comprising a neck portion extending from the distal end of the handle, the neck portion connecting the handle and said upper and lower arms.

9. The device of claim 8, wherein said upper and lower arms are substantially parallel to each, and wherein the parallel upper and lower arms and the neck portion form a u-shape.

10. The device of claim 1, wherein the blade is supported on a rigid member extending between the opposing legs of the lower arm such that a leading edge of the blade protrudes forwardly from the rigid member, and wherein the rigid member is located at about the free ends of the opposing legs of the lower arm.

11. The device of claim 1, wherein the free ends of the opposing legs of the lower arm are pointed so as to pierce through the healthy tissue.

12. The device of claim 1, wherein the free ends of the opposing legs of the lower arm are conical.

13. A fixed depth skin flap elevator device for undermining and separating an even and uniform flap of skin and healthy tissue, at a consistent and controlled depth, from a tissue interior, wherein the tissue interior is below a surface of the skin and includes at least the healthy tissue, the device comprising:
- a blade holder having a substantially u-shaped first structural frame lying substantially in a first plane, said first structural frame having a first end and an opposite second end longitudinally spaced apart on said blade holder,
- a guide having a second structural frame, said second structural frame having opposite first and second ends, wherein the guide is adapted to translate over the surface of the skin during operation of the device,
- said second structural frame overlaying said first structural frame so as to define a spacing gap between at least said first ends of said first and second structural frames, wherein said spacing gap corresponds to a predetermined cutting depth,
- a handle mounted to said second end of said first and second structural frames, and
- a cutting blade rigidly mounted to, so as to extend across, said first end of said first structural frame and fixed relative to said first structural frame so as to lie in a dissection plane, parallel to said first plane, wherein the first end of said first structural frame is adapted to pierce through the healthy tissue of the tissue interior during operation of the device, and
- wherein, during operation of the device, said guide is located over the surface of the skin and said blade holder and said dissection plane are located below the surface of the skin within the tissue interior for piercing and cutting of said healthy tissue in said dissection plane for forming the even and uniform flap of skin and healthy tissue.

14. The device of claim 13, wherein the first end of the first structural frame is an open end, and wherein the second end of the first structural frame is a closed end.

15. The device of claim 13, wherein the second structural frame is substantially u-shaped.

16. The device of claim 15, wherein the first end of the second structural frame is an open end, and wherein the second end of the second structural frame is a closed end.

17. The device of claim 15, wherein said first and second structural frames each have a pair of laterally spaced apart cantilevered arms, mounted to and cantilevered from said second ends of said first and second structural frames, and wherein a spacing gap between the cantilevered arms in the first structural frame is the same as a spacing gap between the cantilevered arms in the first structural frame.

18. The device of claim 13, wherein the first end of the substantially u-shaped first structural frame is pointed.

19. The device of claim 18, wherein the first end protrudes forwardly of the cutting blade.

20. The device of claim 13, wherein the first end of the substantially u-shaped first structural frame is conical.

* * * * *